(12) United States Patent
Ni et al.

(10) Patent No.: US 11,056,250 B1
(45) Date of Patent: Jul. 6, 2021

(54) CONDUCTIVE SURFACE COATING BASED ON MODIFIED AND UNMODIFIED PARTICLES AND METHOD OF PREPARATION THEREOF

(71) Applicant: UNIVERSITY OF NEW BRUNSWICK, Fredericton (CA)

(72) Inventors: Yonghao Ni, Fredericton (CA); Zhibin He, Fredericton (CA); Haihua Wang, Xian (CN)

(73) Assignee: UNIVERSITY OF NEW BRUNSWICK, Fredericton (CA)

( * ) Notice: Subject to any disclaimer, the term of this patent is extended or adjusted under 35 U.S.C. 154(b) by 453 days.

(21) Appl. No.: 15/882,136

(22) Filed: Jan. 29, 2018

Related U.S. Application Data

(63) Continuation of application No. 13/598,027, filed on Aug. 29, 2012, now abandoned.

(60) Provisional application No. 61/528,507, filed on Aug. 29, 2011.

(51) Int. Cl.
| | | |
|---|---|---|
| *H01B 1/12* | (2006.01) | |
| *C09B 67/00* | (2006.01) | |
| *C09B 67/08* | (2006.01) | |
| *H01B 1/10* | (2006.01) | |
| *C07C 50/18* | (2006.01) | |
| *H01B 1/20* | (2006.01) | |
| *H01B 19/02* | (2006.01) | |

(52) U.S. Cl.
CPC .............. *H01B 1/127* (2013.01); *C07C 50/18* (2013.01); *C09B 67/0013* (2013.01); *H01B 1/20* (2013.01); *H01B 19/02* (2013.01)

(58) Field of Classification Search
None
See application file for complete search history.

(56) References Cited

U.S. PATENT DOCUMENTS

| | | | | |
|---|---|---|---|---|
| 3,607,377 A | * | 9/1971 | Cross ................. | G03G 5/101 428/342 |
| 4,214,031 A | * | 7/1980 | Miyakawa .......... | B41M 5/20 427/121 |
| 4,859,246 A | * | 8/1989 | Sennett .............. | C09C 1/42 106/487 |
| 5,108,829 A | * | 4/1992 | Kuhn ................. | C08G 61/124 252/500 |
| 6,132,645 A | * | 10/2000 | Hedges ................ | C08K 9/08 252/510 |
| 6,409,815 B1 | * | 6/2002 | Hennemann ........ | C08K 9/04 106/417 |
| 2008/0142762 A1 | * | 6/2008 | Ni ....................... | H01B 1/127 252/500 |

FOREIGN PATENT DOCUMENTS

| | | |
|---|---|---|
| DE | 102008050932 A1 * | 4/2010 |
| WO | WO 2006/035112 * | 4/2006 |

* cited by examiner

*Primary Examiner* — Tae H Yoon
(74) *Attorney, Agent, or Firm* — Hill & Schumacher

(57) ABSTRACT

Conductive coating compositions and methods of preparation and application thereof are provided, whereby a mixture of conductive polymer encapsulated particles and non-encapsulated particles are employed to provide a conductive surface coating with controllable viscosity and conductivity. The particles may be filler and/or pigment particles such as calcium carbonate or clay, a portion of which are coated with a conductive polymer such as polypyrrole. Encapsulated particles are prepared and filtered, mixed with non-encapsulated particles, and subsequently combined with a binder for application to a surface or substrate such as paper. A dispersant may be included to obtain a suitable viscosity of the mixture prior to application. The relative concentrations of the encapsulated and non-encapsulated particles may be selected to tailor the resulting conductivity of the coating.

18 Claims, No Drawings

CONDUCTIVE SURFACE COATING BASED ON MODIFIED AND UNMODIFIED PARTICLES AND METHOD OF PREPARATION THEREOF

CROSS-REFERENCE TO RELATED APPLICATION

This application is a continuation of U.S. patent application Ser. No. 13/598,027, CONDUCTIVE SURFACE COATING BASED ON MODIFIED AND UNMODIFIED PARTICLES AND METHOD OF PREPARATION THEREOF and filed on Aug. 29, 2012, which claims priority to U.S. Provisional Application No. 61/528,507, titled CONDUCTIVE SURFACE COATING BASED ON MODIFIED AND UNMODIFIED PARTICLES AND METHOD OF PREPARATION THEREOF and filed on Aug. 29, 2011, the entire contents of which are incorporated herein by reference.

BACKGROUND

The present disclosure relates to electrically conductive coatings, and more particularly, the present disclosure relates to electrically conductive composite coatings including conductive polymers.

Electrically conductive composite and coated materials have widespread applications such as electrostatic dissipation, electromagnetic shielding, and energy storage devices. To date, a wide variety of methods have been employed to produce conductive paper, including methods involving the dispersing of conductive fillers such as metal particles, carbon black, graphite or carbon fibers in a polymer matrix, and methods involving the coating of lignocellulosic fibers with conductive polymers and conductive nanomaterials.

Unfortunately, these processes are typically complex, expensive, and are not readily adaptable to existing production methods and equipment. Furthermore, these methods typically fail to deliver a method for producing a conductive coating in a cost-effective manner in which the surface conductivity may be readily controllable.

SUMMARY

Conductive coating compositions, methods of preparation and application thereof are provided, whereby a mixture of conductive polymer encapsulated particles and non-encapsulated particles are employed to provide a conductive surface coating with controllable conductivity and the viscosity of the coating mixture can be controlled. The particles may be filler or pigments such as calcium carbonate or clay, a portion of which are coated with a conductive polymer such as polypyrrole. Encapsulated particles are prepared and filtered, mixed with non-encapsulated particles, and subsequently combined with a binder for application to a surface or substrate such as paper. A dispersant may be included to obtain a suitable viscosity of the mixture prior to application. The relative concentrations of the encapsulated and non-encapsulated particles may be selected to tailor the resulting conductivity of the coating.

Accordingly, in one aspect, there is provided an electrically conductive coating composition comprising non-encapsulated particles and encapsulated particles, wherein the non-encapsulated particles are filler and/or pigment particles, and wherein the encapsulated particles are filler and/or pigment particles that are coated with an electrically conductive polymer, wherein the electrically conductive polymer further includes an organic dopant incorporated therein.

In another aspect, there is provided a mixture for forming an electrically conductive coating, the mixture comprising an aqueous suspension of non-encapsulated particles and encapsulated particles, wherein the non-encapsulated particles are filler and/or pigment particles, and wherein the encapsulated particles are filler and/or pigment particles that are coated with an electrically conductive polymer, wherein the electrically conductive polymer further includes an organic dopant incorporated therein.

In another aspect, there is provided a method of preparing an electrically conductive coating mixture, the method comprising the steps of:

forming a mixture including an aqueous suspension of filler and/or pigment particles, monomers, an oxidant, and an organic dopant;

polymerizing the monomer in the presence of the dopant to form an electrically conductive polymer on the surface of the particles to produce modified particles having the organic dopant incorporated therein;

separating the modified particles;

washing the modified particles; and mixing the separated modified particles with non-encapsulated filler and/or pigment particles to form the electrically conductive coating mixture.

In another aspect, there is provided a mixture for forming an electrically conductive coating, the mixture comprising an aqueous suspension of encapsulated filler and/or pigment particles and one or more of an alkali salt and a dispersant; wherein the encapsulated filler and/or pigment particles are coated with electrically conductive polymer, and wherein the electrically conductive polymer further includes an organic dopant incorporated therein.

A further understanding of the functional and advantageous aspects of the disclosure can be realized by reference to the following detailed description and drawings.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "particle" refers to a particle having a surface suitable for coating with a conductive polymer. Examples of particles include filler or pigment particles. The particles may be porous. Example filler particles include filler particles employed in the paper industry, such as particles of clay and precipitated calcium carbonate. Other paper making particles may also be employed, such as, but not limited to, talc, zeolite and silica gel. Other examples of particles include metal oxide particles.

Electrically conductive coating compositions and methods of their preparation and application are provided as disclosed below. Embodiments provided herein employ a mixture of encapsulated and non-encapsulated particles (i.e. conductive and non-conductive particles), which allows for fine tuning of the coating conductivity. Furthermore, by forming the coating with both encapsulated and non-encapsulated particles, the cost of the coating can be decreased, as a lower quantity of encapsulated particles, and hence a lower amount of conductive polymer, are used in the coating forming process. In some embodiments, additives such as a dispersant may be included in the coating composition to achieve a coating mixture with a viscosity that is suitable for forming a coating layer. The present methods may therefore facilitate improved control of the surface properties of the final products, substantial flexibility in tailor-making the conductive surface layer characteristics associated with a given application, and the ability to separate the production of the electrically conductive particles (for example, in a mixing plant) and the subsequent coating of the surface. In applications involving the coating of paper, the present methods enable the off-site preparation of conductive encapsulated particles, which may be shipped to a separate facility for coating (e.g. using a conventional coating facility).

Electrically conductive coatings are to be formed by combining non-encapsulated particles with particles that are encapsulated with an electrically conductive polymer, and forming a suspension or slurry that can be applied to form a coating on a surface or substrate. In some embodiments, the particles may be filler and/or pigment particles. In one example implementation involving coatings suitable for conductive paper, the particles may include clay particles, such as kaolin clay particles, and the average diameter of the particles may lie within approximately 0.1 to 10 microns. In one example, the particles may include precipitate calcium carbonate particles. In other examples, a suitable range for the particle diameter may be more than 10 microns, or less than 0.1 microns.

The encapsulated particles may be prepared by performing an in-situ polymerization process, in which a monomer is polymerized in the presence of the particles to form an electrically conductive layer on the particles. In one example implementation, the in-situ polymerization process may be performed as follows: particles are mixed with an oxidant, such as ferric chloride or ferric sulphate (or a combination thereof), a dopant, such as anthraquinone-2-sulfonic Acid (AQSA), and a monomer, such as pyrrole. The dopant may be an organic dopant. It is to be understood that although embodiments below disclose chemical polymerization methods for forming the electrically conductive layer on the particles, the electrically conductive layer may also be formed by electrochemical polymerization methods.

In one example implementation, the monomer is pyrrole and the oxidant is ferric chloride ($FeCl_3$), and the pyrrole is polymerized in the presence of a dopant to form an electrically conductive layer of polypyrrole on the particles. The dopant may be a sulfonic acid such as anthraquinone sulfonic acid sodium salt (AQSA-Na). The temperature of the mixture during polymerization may be controlled to a suitable temperature, such as approximately $-10$-$25°$ C. in the present example.

The relative concentrations of the monomer, oxidant, and dopant may be varied in order to vary the properties of the electrically conductive coating on the particles. In the present example, in which the monomer is pyrrole, the oxidant is $FeCl_3$, and the dopant is AQSA, a suitable relative molar concentration of monomer to oxidant to dopant is approximately 1:2:0.3, respectively. In some example formulations, the concentration of monomer prior to initialization of polymerization may range between approximately 0.02 M and 0.09 M. In another example formulation, the molar ratio of oxidant to monomer and molar ratio of dopant to monomer may be approximately 3:1 and approximately 1:3, respectively. In another example formulation, molar ratio of oxidant to monomer may lie between about 1:1 and 4.5:1, and the molar ratio of dopant to monomer may lie between approximately 0.05-1:1. Encapsulated particles having conductivity suitable for a wide range of applications may be prepared by selecting the molar ratio of oxidant to monomer in the range of approximately 2.2-3:1, and a molar range of dopant to monomer in the range of approximately 0.2-0.4:1. In still another example formulation, the dopant to monomer ratio may be approximately 0.25:1. It is to be understood that these example molar ratios are non-limiting, and that the molar ratios employed for forming the encapsulated particles may be varied to some extent, for example, in order to achieve a desired level of conductivity.

As noted above, in selected embodiments, the oxidant may be ferric chloride, ferric sulphate, or a combination thereof. In other example implementations, the oxidant may be one of more of the following: oxygen ($O_2$), ozone ($O_3$), hydrogen peroxide ($H_2O_2$) and other inorganic peroxides, fluorine ($F_2$), chlorine ($Cl_2$), and other halogens, nitric acid ($HNO_3$) and nitrate compounds, sulfuric acid ($H_2SO_4$), persulfuric acids ($H_2SO_5$ and $H_2SO_8$), chlorite, chlorate, perchlorate, and other analogous halogen compounds, hypochlorite and other hypohalite compounds, including household bleach (NaClO), hexavalent chromium compounds such as chromic and dichromic acids and chromium trioxide, pyridinium chlorochromate (PCC), and chromate/dichromate compounds, permanganate compounds, sodium perborate, nitrous oxide ($N_2O$), silver oxide ($Ag_2O$), osmium tetroxide ($OsO_4$), Tollens' reagent, and 2,2'-dipyridyldisulfide (DPS).

In addition to the conductive polymer disclosed above, other suitable conductive polymers include polyacetylene, polypyrrole, and polyaniline. Other alternatives include poly (fluorene)s, polyphenylenes, polypyrenes, polyazulenes, polynaphthalenes, polycarbazoles, polyindoles, polyazepines, poly(thiophene)s (PT), poly(3,4-ethylenedioxythiophene) (PEDOT), poly(p-phenylene sulfide) (PPS), poly(acetylene)s (PAC), and poly(p-phenylene vinylene) (PPV). Furthermore, alternative dopants include 2-naphthalene sulfonic acid, dodecyl benzensulfonic acid sodium salt, anthraquinone-2-sulfonic acid, AOT (sodium bis(2-ethylhexyl) sulfosuccinate), and other sulfonic acids or their sodium or other salts (chloride, perchlorate, sulfonate).

The polymerization reaction is allowed to proceed in order to obtain an electrically conductive layer of a desired thickness on the particles. In the present example, the reaction may be allowed to proceed for approximately 2 to 3 hours after the addition of the pyrrole and AQSA. The composition of the reaction mixture and the reaction time may be varied in order to obtain a desired deposition thickness of electrically conductive polymer on the particles. In examples provided below, the relative amount of electrically conductive polymer to the total weight of an encapsulated particle may be approximately 1-30%.

After having formed the electrically conductive and polymer encapsulated particles, the encapsulated particles are separated from the reaction mixture. For example, the encapsulated particles may be collected by filtration or centrifugation and washed by a suitable wash liquid, such as water. The washing of the encapsulated particles may be performed by diluting the reaction mixture in water, and subsequently dewatering the diluted mixture, for example, by centrifugation or filtration. The dilution and dewatering steps may be repeated one or more times in order to achieve a suitable level of purification. The washed encapsulated particles may be stored prior to use in an aqueous suspension, such as a suspension with a solid content of approximately 40% by weight.

Having produced the encapsulated particles, they are then mixed with non-encapsulated particles in order to prepare a mixture consisting of an aqueous suspension or slurry of encapsulated and non-encapsulated particles. The suspension may include solvents other than water. The relative amounts of encapsulated and non-encapsulated particles may vary depending on the desired conductivity of the coatings that are to be produced from the mixture. In some example implementations, the ratio of encapsulated particles to the total number of particles (by weight) may range from approximately 5% to 100%. In other applications, it may be desirable for the coating to be formed with a relative weight of less than 5% (for higher resistivity coatings). The relative weight of the particles (both encapsulated and non-encapsulated) may vary depending on the desired properties of the coating mixture (such as its viscosity), and a suitable range for a wide variety of applications is approximately 10-75%.

It is to be understood that the coating composition and/or coating mixture may be formed with more than one type, or composition, of particles. The non-particles, and/or the particles that are coated to form the coated/modified particles, may include two or more different groups of particles, where the different groups of particles have different compositions. For example, the non-encapsulated and/or encapsulated particles may include a combination of different filler particles, different pigment particles, and/or a mixture of one or more compositions of filler and pigment particles. Furthermore, the encapsulated particles may include particles having different coatings, such as coatings having different compositions, and/or different coating thicknesses. In one example implementation, the encapsulated particles may include both different particle compositions and different compositions of the coatings. The different particle composition, and/or composition of the coating applied to the particles, may be employed to tailor one or more aspects or properties of the overall coating composition, such as the conductivity, brightness, weight, and/or cost. The mixture and subsequent coating composition may further include a binder. Suitable binders include, but are not limited to, polyvinylidene fluoride (PVdF), carboxymethyl cellulose (CMC) rubber, natural polyisoprene: cis-1,4-polyisoprene natural rubber (NR) and trans-1,4-polyisoprene gutta-percha, synthetic polyisoprene (IR: isoprene rubber); polybutadiene (BR: butadiene rubber); chloroprene rubber (C; polychloroprene, neoprene, Baypren® etc.), butyl rubber (copolymer of isobutylene and isoprene, IIR), halogenated butyl rubbers (chloro butyl rubber: CIIR; bromo butyl rubber: BIIR); styrene-butadiene rubber (copolymer of styrene and butadiene, SBR); nitrile rubber (copolymer of butadiene and acrylonitrile, NBR, also called Buna N rubbers), hydrogenated nitrile rubbers (HNBR; Therban® and Zetpol®), EPM (ethylene propylene rubber, a copolymer of ethylene and propylene), EPDM rubber (ethylene propylene diene rubber, a terpolymer of ethylene, propylene and a diene-component), epichlorohydrin rubber (ECO), polyacrylic rubber (ACM, ABR), silicone rubber (SI, Q, VMQ), fluorosilicone rubber (FVMQ), fluoroelastomers (FKM, and FEPM; Viton®, Tecnoflon®, Fluorel®, Aflas® and Dai-El®, perfluoroelastomers (FFKM; Tecnoflon PFR®, Kalrez®, Chemraz®, Perlast®), Polyether block amides (PEBA), chlorosulfonated polyethylene (CSM; Hypalon®), ethylene-vinyl acetate (EVA), thermoplastic elastomers (TPE), the proteins resilin and elastin, and polysulfide rubber, latex, starch clay, and or similar pigments/binders.

In some cases, it may be beneficial to include additives to further control the properties of the coating mixture and/or the coating that is formed after application of the coating mixture to a surface or substrate. In one embodiment, a dispersant is added to the coating mixture to lower and/or control the viscosity of the coating mixture. The viscosity control additive is provided in an amount such that the Brookfield viscosity of the electrical conductive coating mixture of less than 4000 mPa·s and greater than 310 mPa·s. In some applications, it can be important to provide a mixture with a sufficiently low viscosity to pour the coating mixture and subsequently form a uniform coating. Suitable yet non-limiting dispersants include sodium dodecyl sulfate, detergents, anionic polymers, aryl-alkyl derivative of sulfonic acid, polyphosphates, lignosulfonates, quebracho tannins, and various water-soluble synthetic polymers. Other suitable additives include lubricants and water retention agents, such as CMC and starch, and/or any one or more of cellulose ethers, superabsorbent polymers (SAP), polyacrylamide, copolymer, ethylene maleic anhydride copolymer, cross-linked carboxymethylcellulose, polyvinyl alcohol copolymers, cross-linked polyethylene oxide, starch grafted copolymer of polyacrylonitrile sodium polyacrylate, acrylonitrile, acrylic acid, acrylamide and polyvinyl alcohol.

As described in the Examples below, an alkali salt, such as sodium bicarbonate, may be added to the coating mixture to control the pH and decrease the viscosity of coating dispersion. The pH range can be from 4 to 8, preferably 4.5 to 7, more preferably from 5 to 6.5. Sodium bicarbonate is a suitable chemical for this purpose, but other chemicals may include weak alkali sources, such as magnesium oxide/hydroxide, salts made of strong alkali but weak acid, such as calcium carbonate, sodium carbonate, and sodium or potassium phosphates.

The mixture containing the electrically conductive encapsulated particles and the non-encapsulated particles may then be cast onto a surface or substrate to form the electrically conductive coating. In one embodiment, the surface is paper, and the coating is applied to the paper to produce electrically conductive paper.

In one example, the substrate is a base paper sheet. An example paper sheet may have a basis weight of 100 grams per square meter, and the furnish may consist of softwood and hardwood kraft pulp, high-yield pulp and recycled fibers. The coating mixture is prepared to have a solid content in the range of 50 to 70% by weight, and the mixture is produced with a viscosity of about 1200 m Pa·s (Brookfield, at 100 rpm). As noted above, the viscosity may be controlled and/or lowered by the addition of a dispersant to the coating mixture prior to its application. The pigment composition includes the encapsulated conductive particles and unmodified particles, and the relative amount of encapsulated particles and non-encapsulated particles is selected to achieve a desired electrical conductivity of the coating. A suitable particle ratio for a given application may be determined through experimentation and/or calibration of the process.

The amount of coating material applied to the surface or substrate may vary as per the requirements of the application. In one example in which the substrate is paper, the quantity of applied coating may range between about 4 to 20 grams per square meter.

The coating mixture can be applied according to known coating methods and using commercial coating equipment. For example, the coating mixture can be applied using blade, notch, spray, and spin coating methods. Commercially available coating equipment suitable with the present method includes, but is not limited to, rod coaters, knife coaters, and curtain coaters.

After having coated the substrate, the coating is allowed to dry, or dried in a controlled thermal environment. The coating may also be conditioned in an environment with a controlled temperature or humidity. In one example implementation in which the coating mixture is applied to paper to form conductive paper, the coated paper may be processed by drying the coated paper in an oven at a temperature of about 105° C. for approximately 2 minutes, and then conditioned in an environment of about 23° C. and about 50% relative humidity for approximately 4 hours.

It is to be understood that the coating composition may be controlled by varying the preceding process steps and process chemicals in order to obtain a coating composition with a preferred cost and electrical conductivity. The production cost is largely dictated by the thickness of the coating layer and the relative quantity of encapsulated and non-encapsulated particles. The electrical conductivity may be controlled by varying the process chemicals and their quantities, and surface conductivities ranging from $10^3$ to $10^9$ ohm may be achieved. Finally, it is noted that the performance of the coatings may also be affected by the uniformity of the surface application layer.

One advantageous aspect of the methods disclosed herein is that the conductive particles, such as conductive fillers or pigments, can be produced on a commercial scale in a plant, independent of the manufacturing of the substrate to which to coating is to be applied (e.g. paper), so that a large quantity of particles can be produced in a centralized plant (such as a filler/mixing plant), which may be subsequently shipped to another facility (e.g. a coating facility). This process is advantageous in comparison with on-site polymerization of pulp fibers and provides a comparable decrease in the overall production cost.

While the preceding disclosure has been illustrated referring to examples involving conductive paper, it is to be understood that the coating compositions disclosed above, and their methods of preparation and application, may be applied to a wide range of surfaces and substrates. For example, other materials suitable to be coated according to the present methods include: plastic sheets (to provide conductivity, e.g. for electroplating), metal sheets (e.g. for anti-corrosion applications), wood (e.g. conductive, hard wood floors for anti-static), cement (conductive/anti-static/EMI), ceramic/tile/laminate (conductive/anti-static), brick (anti-static, EMI), dry-wall (EMI), countertops (anti-static), and cloth fibers (anti-static), woven and non-woven material, made of natural fibers, synthetic fibers, and their mixtures.

Furthermore, a wide variety of products and applications may be addressed by the compositions and methods disclosed herein. For example, metal-oxide particles may be coated with pyrrole for battery applications (e.g. $LiFePO_4$) according to the aforementioned methods. Other products and devices that may be produced according to the methods disclosed above include antistatic coatings and packaging, paper-based electrodes, energy storage devices (capacitors and batteries), sensors, fuel cells, conductive and absorptive materials for biological and/or in-vitro diagnostic devices, heating elements, antennas, electromagnetic shields and Faraday cages, security and anti-counterfeiting paper, radio frequency identification tags, substrates for electroluminescent molecules (where the conductive coating is in electrical communication with the electroluminescent molecules), conductive paper for electrostatic measurements, anti-static weigh boats, and electrically conductive filtration devices.

The method disclosed above, and the examples below, provide embodiments and examples involving the application of a coating mixture to a surface or substrate to form an electrically conductive coating. It is to be understood that the coating need not cover the entire surface or substrate, and that the present disclosure further contemplates partially coated surfaces or substrates. In one example, the multiple regions of a surface may be coating to form electrically isolated conducting regions, which may be useful as surface electrodes. This may be achieved by treating only certain areas of the surface (e.g. applying a spray, drop, drip, or other surface pattern), screen printing, ink-jet printing, sizing, dripping, or repeating the coating procedure more than once.

Alternatively or additionally, the electrical conductivity of a given coating region need not be constant through the region, and may instead vary spatially over the region or a portion thereof. This may be achieved, for example, by linearly changing the concentration of conductive particles during deposition (e.g. add more and more conductive particles to the slurry).

As shown in the examples below, selected implementations may provide surface conductivities below 1000 kOhm/sq, or below 100 kOhm/sq, below 10 kOhm/sq, and below 1 kOhm/sq.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1: Preparation and Application of Conductive Coating

Equivalent to 2000 g dry solid of kaolin clay slurry (about 70% solid content), 2000 g water and 342 g of anthraquinone sulfonic acid sodium salt (AQSA) were mixed in a 30-quart Hobart mixer for 30 minutes. Next, 2420 g of ferric chloride hexahydrate dissolved in 3000 g water was added, and mixed in the same Hobart mixer for another 60 minutes. Then 200 g pyrrole dissolved in 4000 g water was charged to the mixer, and the polymerization of pyrrole started and the reaction continued for 3 hours under continuous mixing in the Hobart mixer. The polymerization of pyrrole occurred in the presence of clay, thus, the in-situ formed polypyrrole is deposited on the surface of the clay particles. Throughout the polymerization reaction, the temperature of the content was maintained at about 20° C. At the end of the reaction, the content of the mixer was diluted with 10 kg water and subsequently dewatered to about 40% solid content by centrifugation. The solid was further processed by dilution/centrifugation with 10 kg of water each time, and centrifuged to about 40% solid. The product was noted as "10%-polypyrrole modified clay".

The 10%-polypyrrole modified clay prepared above was mixed with the unmodified clay at various ratios to make a clay dispersion of 40 to 70% total solid content. The results showed that the addition of the polypyrrole modified clay caused the viscosity of the clay dispersion to increase dramatically, as shown in Table 1. Therefore, it is of practical importance to find effective additives (dispersant to decrease the viscosity) so that conventional coating technologies can be used to apply the mixture of polypyrrole modified clay and unmodified clay onto the paper surface.

TABLE 1

| Polypyrrole modified clay, % | Un-modified clay, % | Solid content of the mixture, % | Brookfield viscosity, mPas | Flow ability |
| --- | --- | --- | --- | --- |
| 0 | 100 | 70 | 420 | Good |
| 0 | 100 | 60 | 30 | Good |
| 10 | 90 | 60 | 5850 | Poor |
| 15 | 85 | 60 | >1,000,000 | Poor |
| 0 | 100 | 40 | 10 | Good |
| 10 | 90 | 40 | 90 | Good |
| 20 | 80 | 40 | 1,010 | Good |
| 30 | 70 | 40 | 3,360 | ok |
| 40 | 40 | 40 | 904,000 | poor |

Example 2: Addition of Sodium Lignosulfonate as Dispersant

A clay dispersion made of the 10%-polypyrrole modified clay and unmodified clay was prepared as in Example 1, except that sodium lignosulfonate was added in some cases to decrease the viscosity. As shown in Table 2, the sodium lignosulfonate was very effective in decreasing the viscosity. With 0.8 to 1.2% sodium lignosulfonate, the dispersion had good viscosity and flow property under the conditions.

TABLE 2

| Lignin sulfonate, % | Polypyrrole modified clay, % | Un-modified clay, % | Solid content of the mixture, % | Brookfield viscosity, mPaS | Flow ability |
| --- | --- | --- | --- | --- | --- |
| 0 | 10 | 90 | 60 | 5850 | poor |
| 1.2 | 10 | 90 | 60 | 1620 | good |
| 0 | 15 | 85 | 60 | >1,000,000 | non |
| 1.2 | 15 | 85 | 60 | 47,600 | poor |
| 0 | 40 | 60 | 40 | 904,000 | poor |
| 0.1 | 40 | 60 | 40 | 6,230 | poor |
| 0.2 | 40 | 60 | 40 | 4,710 | poor |
| 0.4 | 40 | 60 | 40 | 2,120 | ok |
| 0.8 | 40 | 60 | 40 | 830 | good |
| 1.2 | 40 | 60 | 40 | 540 | good |
| 1.6 | 40 | 60 | 40 | 530 | good |

Example 3: Addition of Polystyrene Sulfonic Acid as Dispersant

A clay dispersion made of 40% of the 10%-polypyrrole modified clay and 60% unmodified clay was prepared as in Example 1, except that polystyrene sulfonic acid was added to decrease the viscosity. As shown in Table 3, polystyrene sulfonic acid was also effective in decreasing the viscosity.

TABLE 3

| Polystyrene sulfonic acid, % | Polypyrrole modified clay, % | Un-modified clay, % | Solid content, % | Brookfield viscosity, mPaS | Flow ability |
| --- | --- | --- | --- | --- | --- |
| 0 | 40 | 60 | 40 | 904,000 | poor |
| 0.1 | 40 | 60 | 40 | 5,180 | poor |
| 0.2 | 40 | 60 | 40 | 3,120 | ok |
| 0.4 | 40 | 60 | 40 | 1,460 | ok |
| 0.8 | 40 | 60 | 40 | 850 | good |
| 1.2 | 40 | 60 | 40 | 1020 | good |

Example 4: Surface Conductivity of Coatings Based on 5%-Polypyrrole Modified Clay 5%-polypyrrole modified clay was prepared by in-situ polymerization with 5% pyrrole (based on clay), according to the procedures in Example 1, except that the amounts of AQSA, ferric chloride and pyrrole were reduced accordingly and proportionally.

A conductive coating dispersion was then prepared as follows. The coating formula contained equivalent to 12.5 to 100 parts of 5%-polypyrrole modified clay, 87.5 to 0 parts of unmodified clay (as 70% dispersion), 1.2 parts of sodium ligninsulfonate as dispersant, 10 parts of latex (DOW-638NA), 0.5 part of calcium stearate as lubricant, and 1.0 parts of carboxy-methyl cellulose (Finnex 10G) as water retention agent. The final coating dispersion had about 40% total dry solids. The coating dispersion was applied to a paper surface on a lab coater (K303 Multicoater), operated at 10 m/min with a #4 spiral metering rod. The coated paper was dried in an oven at 105° C. for 2 minutes, and then conditioned in an environment of 23° C. and 50% relative humidity for 4 hours. Then the surface resistivity of the coated paper was measured using a Trek 152-1-CE electrical resistance meter with a Trek 152P-CR-1-CE concentric probe. The surface resistivity of the paper coated with the coating dispersion of different composition was presented in Table 4.

TABLE 4

| Polypyrrole modified clay, % | Un-modified clay, % | Total coating amount applied, g/m$^2$ | Pyrrole usage, g/m$^2$ | Surface resistivity, kΩ/sq. |
| --- | --- | --- | --- | --- |
| 12.5 | 87.5 | 9.9 | 0.052 | 3,060,000 |
| 15 | 85 | 12.4 | 0.077 | 2,240,000 |
| 20 | 80 | 11.3 | 0.094 | 2,290,000 |
| 30 | 70 | 11.8 | 0.148 | 1,780,000 |
| 50 | 50 | 10.7 | 0.222 | 2,120 |
| 60 | 40 | 11.0 | 0.274 | 86.6 |
| 70 | 30 | 10.5 | 0.307 | 29.4 |
| 100 | 0 | 7.92 | 0.330 | 7.86 |

Example 5: Surface Conductivity of Coatings Based on 10%-Polypyrrole Modified Clay 10%-polypyrrole modified clay was prepared by in-situ polymerization with 10% pyrrole (based on clay), according to the procedures in Example 1. A conductive coating dispersion was prepared as follows. The coating formulation contained equivalent to 12.5 to 70 parts of the 10%-polypyrrole modified clay, 87.5 to 30 parts of un-modified kaolin clay (as 70% dispersion), 1.2 parts of sodium ligninsulfonate (Tembec ARBO S01P) as dispersant, 10 parts of latex (DOW-638NA), 0.5 part of calcium stearate as lubricant, and 1.0 parts of carboxy-methyl cellulose (Finnex 10G) as water retention agent. The final coating dispersion had about 40% total dry solids. The coating dispersion was applied to a paper surface on a lab coater (K303 Multicoater), operated at 10 m/min with a #4 spiral metering rod. The coated paper was dried in an oven at 105° C. for 2 minutes, and then conditioned in an environment of 23° C. and 50% relative humidity for 4 hours. Then the surface resistivity of the coated paper was measured using a Trek 152-1-CE electrical resistance meter with a Trek 152P-CR-1-CE concentric probe. The surface resistivity of the paper coated with the coating dispersion of different composition was presented in Table 5.

TABLE 5

| Poly-pyrrole modified clay, % | Un-modified clay, % | Total coating amount applied, g/m$^2$ | Pyrrole usage, g/m$^2$ | Surface resistivity, kΩ/sq. |
|---|---|---|---|---|
| 12.5 | 87.5 | 9.4 | 0.098 | 2,400,000 |
| 15 | 85 | 9.7 | 0.121 | 2,190,000 |
| 20 | 80 | 12.3 | 0.206 | 537,000 |
| 30 | 70 | 12.9 | 0.322 | 27.5 |
| 50 | 50 | 10.6 | 0.441 | 6.89 |
| 60 | 40 | 10.4 | 0.520 | 3.21 |
| 70 | 30 | 10.2 | 0.598 | 1.29 |

Example 6: Surface Conductivity of Coatings Based on

20%-Polypyrrole Modified Clay 20%-polypyrrole modified clay was prepared by in-situ polymerization with 20% pyrrole (based on clay), according to the procedures in Example 1, except that the amounts of AQSA, ferric chloride and pyrrole were increased accordingly and proportionally.

A conductive coating dispersion was prepared as follows. The coating formulation contained equivalent to 12.5 to 30 parts of the 20%-polypyrrole modified clay, 87.5 to 70 parts of un-modified kaolin clay (as 70% dispersion), 1.2 parts of sodium ligninsulfonate (Tembec ARBO S01P) as dispersant, 10 parts of latex (DOW-638NA), 0.5 part of calcium stearate as lubricant, and 1.0 parts of carboxy-methyl cellulose (Finnex 10G) as water retention agent. The final coating dispersion had about 40% total dry solids. The coating dispersion was applied to a paper surface on a lab coater (K303 Multicoater), operated at 10 m/min with a #4 spiral metering rod. The coated paper was dried in an oven at 105° C. for 2 minutes, and then conditioned in an environment of 23° C. and 50% relative humidity for 4 hours. Then the surface resistivity of the coated paper was measured using a Trek 152-1-CE electrical resistance meter with a Trek 152P-CR-1-CE concentric probe. The surface resistivity of the paper coated with the coating dispersion of different composition was presented in Table 6.

TABLE 6

| Poly-pyrrole modified clay, % | Un-modified clay, % | Total coating amount applied, g/m$^2$ | Pyrrole usage, g/m$^2$ | Surface resistivity, kΩ/sq |
|---|---|---|---|---|
| 12.5 | 87.5 | 9.9 | 0.206 | 768,000 |
| 15 | 85 | 9.0 | 0.226 | 44.5 |
| 20 | 80 | 9.1 | 0.304 | 10.5 |
| 30 | 70 | 9.8 | 0.490 | 2.87 |

Example 7: Surface Conductivity of Coatings Based on 30%-Polypyrrole Modified Clay 30%-polypyrrole modified clay was prepared by in-situ polymerization with 30% pyrrole (based on clay), according to the procedures in Example 1, except that the amounts of AQSA, ferric chloride and pyrrole were increased accordingly and proportionally.

A conductive coating dispersion was then prepared as follows. The coating formulation contained equivalent to 12.5 to 30 parts of the 30-% polypyrrole modified clay, 87.5 to 70 parts of un-modified kaolin clay (as 70% dispersion), 1.2 parts of sodium ligninsulfonate (Tembec ARBO S01P) as dispersant, 10 parts of latex (DOW-638NA), 0.5 part of calcium stearate as lubricant, and 1.0 parts of carboxy-methyl cellulose (Finnex 10G) as water retention agent. The final coating dispersion had about 40% total dry solids. The coating dispersion was applied to a paper surface on a lab coater (K303 Multicoater), operated at 10 m/min with a #4 spiral metering rod. The coated paper was dried in an oven at 105° C. for 2 minutes, and then conditioned in an environment of 23° C. and 50% relative humidity for 4 hours. Then the surface resistivity of the coated paper was measured using a Trek 152-1-CE electrical resistance meter with a Trek 152P-CR-1-CE concentric probe. The surface resistivity of the paper coated with the coating dispersion of different composition was presented in Table 7.

TABLE 7

| Poly-pyrrole modified clay, % | Un-modified clay, % | Total coating amount applied, g/m$^2$ | Pyrrole usage, g/m$^2$ | Surface resistivity, kΩ/sq. |
|---|---|---|---|---|
| 12.5 | 87.5 | 10.5 | 0.329 | 560,000 |
| 15 | 85 | 11.1 | 0.416 | 33.7 |
| 20 | 80 | 9.8 | 0.489 | 9.65 |
| 30 | 70 | 10.8 | 0.807 | 2.52 |

Example 8: Use of Ferric Chloride and/or Ferric Sulphate as Oxidant 20 g of cellulose pulp fibers were added with deionized water into a 2-liter Hobart mixer to make a pulp slurry of 15% consistency. 2.89 g of anthraquinone-2-sulfonic acid sodium salt (AQSA) was added to the pulp slurry and mixed for 10 minutes. Then various amount of oxidant (ferric chloride or ferric sulphate) was added and mixed for another 10 minutes, followed by the addition of 2.4 grams of freshly distilled pyrrole to start the in-situ polymerization that lasted for 30 minutes.

During the reaction, the temperature was maintained at 0° C. using an ice bath. By the end of the reaction, the cellulose fibers turned into a dark black color due to the deposition of polypyrrole on the fibers. The polypyrrole-modified fibers were washed then with 2 liters of de-ionized water and made into lab paper sheets of 100 g/m² that were dried at 23 degree C. and 50% RH. The paper sheets were cut into 15 mm wide strips and tested for surface resistivity with a Keithley multimeter. The results were summarized in Tables 8 and 9. Additional results are provided in Table 10 showing the effect of the molar ratio of pyrrole to FeCl₃ to dopant, where AQSA and/or AOT (sodium bis(2-ethylhexyl) sulfosuccinate) are employed as dopants.

The same process, involving the use of ferric chloride and/or ferric sulphate, may be applied in the formation of a conductive polymer layer on a particle, as described in the preceding embodiments.

TABLE 8

Effect of oxidant type and dosage on the surface resistivity of resultant paper composite

| Trial # | Oxidant | Molar ratio of oxidant/pyrrole | Surface resistivity (kΩ/square) |
|---|---|---|---|
| 1 | FeCl₃ | 1.0 | 27.0 |
| 2 | FeCl₃ | 2.0 | 1.33 |
| 3 | FeCl₃ | 3.0 | 0.63 |
| 4 | FeCl₃ | 4.0 | 0.53 |
| 5 | Fe₂(SO₄)₃ | 1.0 | 3400 |
| 6 | Fe₂(SO₄)₃ | 2.0 | 31.8 |
| 7 | Fe₂(SO₄)₃ | 3.0 | 10.3 |
| 8 | Fe₂(SO₄)₃ | 4.0 | 8.00 |

(Note: Pyrrole dosage was 12% weight of cellulose fibers, and the molarmratio of AQSA to pyrrole was 0.26)

TABLE 9

Effect of combined oxidants of FeCl₃ and Fe₂(SO₄)₃ on the surface resistivity of resultant paper composite

| Trial # | Molar ratio of FeCl₃ to pyrrole | Molar ratio of Fe₂(SO₄)₃ to pyrrole | Surface resistivity (kΩ/square) |
|---|---|---|---|
| 9 | 0 | 4 | 31.7527 |
| 10 | 1 | 3 | 18.6041 |
| 11 | 2 | 2 | 10.9757 |
| 12 | 3 | 1 | 7.6815 |
| 13 | 4 | 0 | 1.3275 |

(Note: Pyrrole dosage was 12% weight of cellulose fibers, and the molar ratio of AQSA to pyrrole was 0.26)

TABLE 10

Effect of pyrrole and dopant dosage on the surface resistivity

| Trial # | Pyrrole dosage, % on fibers | Dopant type | Molar ratio of pyrrole/FeCl3/dopant | Surface resistivity (kΩ/sq) |
|---|---|---|---|---|
| 14 | 12 | AQSA | 1/2/0.26 | 1.3275 |
| 15 | 12 | AOT | 1/2/0.26 | 0.5451 |
| 16 | 20 | 80%AQSA + 20% AOT | 1/3.5/0.3 | 0.1930 |
| 17 | 20 | 80%AQSA + 20% AOT | 1/4.5/0.3 | 0.2153 |

(*AOT is sodium bis(2-ethylhexyl) sulfosuccinate and used as dopant.)

Example 9: Preparation of Coating without pH Control

A conductive coating dispersion was prepared by mixing equivalent to 50 parts of the 10%-polypyrrole modified clay, 50 parts of un-modified Kaolin clay, 1.2 parts of sodium ligninsulfonate (Tembec ARBO S01P) as dispersant, 10 parts of latex (DOW-638NA) as binder, 0.5 parts of calcium stearate as lubricant, and 1.0 parts of carboxy-methyl cellulose (Finnex 10G) as water retention agent. The final coating dispersion had about 34.4% total dry solids, pH of 4.16 and Brookfield viscosity of 3500 cp. The coating dispersion was applied to a paper surface on a lab coater (K303 Multicoater), operated at 10 m/min with a #4 spiral metering rod at a coating amount of 15 g/m². The coated paper was dried in an oven at 105° C. for 2 minutes, and then conditioned in an environment of 23° C. and 50% relative humidity for 4 hours. Then the surface resistivity of the coated paper was measured using a Trek 152-1-CE electrical resistance meter with a Trek 152P-CR-1-CE concentric probe. The surface resistivity of the coated paper was 3,700 Ohm/sq.

Example 10: Formation of Coatings with pH Control Via Addition of Weak Alkali Salts/Sources In the present example, it is shown that the addition of sodium bicarbonate can decrease the viscosity of the coating formula. The same coating dispersion was prepared as in the preceding example, except that 0.5 part of sodium bicarbonate was added for the purpose of decreasing the viscosity. The pH of the dispersion was 5.85, and its Brookfield viscosity was 1070 cp. The surface resistivity of the resulting product was 2,600 ohm/sq.

A conductive coating dispersion was prepared by mixing equivalent to 30 parts of the 10%-polypyrrole modified clay, 70 parts of un-modified Kaolin clay, 0.3 parts of sodium ligninsulfonate (Tembec ARBO S01P) as dispersant, 10 parts of latex (DOW-638NA) as binder, 0.5 part of calcium stearate as lubricant, and 1.0 parts of carboxy-methyl cellulose (Finnex 10G) as water retention agent. The final coating dispersion had about 40.4% total dry solids, pH of 4.50 and Brookfield viscosity of 1630 cp. The coating dispersion was applied to a paper surface. The surface resistivity of the coated paper was 85,000 ohm/sq.

Sodium bicarbonate was then employed to decrease the viscosity of the coating dispersion under otherwise the same conditions as above. 0.25 part of sodium bicarbonate was added. The pH of the dispersion was 6.15, and its Brookfield viscosity was 310 cp. The coating dispersion was applied to the paper surface. The surface resistivity of the coated product was 40,000 ohm/sq.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of preparing an electrically conductive coating mixture, the method comprising the steps of:
   forming a mixture including an aqueous suspension, the mixture comprising:
      one or more of filler particles and pigment particles;
      monomers;
      an oxidant; and
      an organic dopant;
   polymerizing the monomer in the presence of the organic dopant to form an electrically conductive polymer on the surface of the particles to produce encapsulated particles having the organic dopant incorporated therein;

separating the encapsulated particles;

washing the encapsulated particles;

mixing the encapsulated particles with non-encapsulated filler particles and/or pigment particles in an aqueous suspension to form the electrically conductive coating mixture; and decreasing the viscosity of the electrically conductive coating mixture by adding a viscosity control additive comprising one or more of sodium bicarbonate and a weak alkali;

wherein the viscosity control additive is provided in an amount such that the pH of the electrically conductive coating mixture is between 3.5 and 8; and wherein the viscosity control additive is provided in an amount such that the Brookfield viscosity of the electrically conductive coating mixture is less than 4000 mPa·s and greater than 310 mPa·s.

2. The method according to claim 1 wherein the weak alkali is selected from the group consisting of sodium carbonate, magnesium oxide, magnesium hydroxide, sodium phosphate, and potassium phosphate.

3. The method according to claim 1 wherein the viscosity control additive is provided in an amount such that the pH of the electrically conductive coating mixture is between 4.5 and 7.

4. The method according to claim 1 wherein the viscosity control additive is provided in an amount such that the pH of the electrically conductive coating mixture is between 5 and 6.5.

5. The method according to claim 1 further comprising adding sodium lignosulfonate to further decrease the viscosity of the electrically conductive coating mixture.

6. The method according to claim 5 wherein a solid content of the electrically conductive coating mixture is less than or equal to 40%, and wherein the encapsulated particles comprise less than 40% of the total quantity of particles, and wherein the amount of sodium lignosulfonate is greater than or equal to 0.4% of the electrically conductive coating mixture by weight.

7. The method according to claim 1 wherein the organic dopant is anthraquinone sulfonic acid.

8. The method according to claim 1 wherein the non-encapsulated particles include two or more different groups of non-encapsulated particles, and wherein the different groups of non-encapsulated particles have different compositions.

9. The method according to claim 1 wherein the encapsulated particles include two or more different groups of encapsulated particles, and wherein the particles of at least two different groups of encapsulated particles have different compositions.

10. The method according to claim 1 wherein the encapsulated particles include two or more different groups of encapsulated particles, and wherein the coatings of at least two different groups of encapsulated surface modified particles have different compositions.

11. The method according to claim 1 wherein a solid content of the electrically conductive coating mixture is between 40% and 60%, and wherein the encapsulated particles comprise 10% to 40% of the total quantity of particles.

12. The method according to claim 1 wherein the encapsulated particles include approximately 5 to 30% of electrically conductive polymer by weight.

13. The method according to claim 1 wherein a ratio of the weight of the encapsulated particles to the total weight of the non-encapsulated particles and the encapsulated particles is approximately 5% to 95%.

14. The method according to claim 1 wherein the non-encapsulated particles and/or the encapsulated particles comprise clay particles.

15. The method according to claim 1 wherein the non-encapsulated particles are selected from the group consisting of precipitated calcium carbonate, talc, zeolite, and silica particles.

16. The method according to claim 1 wherein the electrically conductive polymer is selected from the group consisting of polyacetylene, polypyrrole, and polyaniline.

17. The method according to claim 1 further comprising the steps of:

applying the electrically conductive coating mixture to a surface and forming a conductive coating on the surface; and drying the conductive coating.

18. The method according to claim 17 further comprising, after drying the conductive coating, conditioning the conductive coating in an environment with a controlled relative humidity and temperature.

* * * * *

UNITED STATES PATENT AND TRADEMARK OFFICE
CERTIFICATE OF CORRECTION

| | | |
|---|---|---|
| PATENT NO. | : 11,056,250 B1 | Page 1 of 1 |
| APPLICATION NO. | : 15/882136 | |
| DATED | : July 6, 2021 | |
| INVENTOR(S) | : Yonghao Ni et al. | |

It is certified that error appears in the above-identified patent and that said Letters Patent is hereby corrected as shown below:

In the Claims

Column 16, Line 13 Claim 10 Should read:
10. The method according to claim 6 wherein the encapsulated particles include two or more different groups of encapsulated particles, and wherein the coatings of at least two different groups of encapsulated particles have different compositions.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*